United States Patent [19]

Skubich et al.

[11] 4,205,904
[45] Jun. 3, 1980

[54] DETECTION AND INDICATION DEVICE

[75] Inventors: Otto Skubich, Hanover; Rudolf Perkert, Seelze; Karl-Heinz Fischer, Laatzen, all of Fed. Rep. of Germany

[73] Assignee: Massey-Ferguson Services N.V., Curacao, Netherlands Antilles

[21] Appl. No.: 959,951

[22] Filed: Nov. 13, 1978

[30] Foreign Application Priority Data

Nov. 18, 1977 [GB] United Kingdom ............... 48016/77

[51] Int. Cl.² .............................................. G08B 21/00
[52] U.S. Cl. ................................ 340/631; 200/61.09; 210/85
[58] Field of Search ............................... 340/627, 631; 200/61.09; 210/85, 86, 93, 493 B, 497 R

[56] References Cited
U.S. PATENT DOCUMENTS

| 3,186,549 | 6/1965 | Botstiber | 210/86 |
| 3,553,672 | 2/1968 | Smith | 340/627 |

*Primary Examiner*—John W. Caldwell, Sr.
*Assistant Examiner*—Daniel Myer
*Attorney, Agent, or Firm*—William R. Nolte

[57] ABSTRACT

A device for indicating the presence of electrically conducting particles, such as metal detritus, in a liquid such as hydraulic oil passing through a filter in which a gap is provided adjacent the filter into which metal particles are swept by the liquid flow to form a conducting bridge in an electrical circuit. In a preferred embodiment, an annular gap closed to through flow is provided between an insulated metal ring around a filter element and the wall of the flow passage surrounding the filter, and the ring and the wall are connected to an electrical circuit for actuating a warning light or audible alarm when the gap is bridged.

8 Claims, 1 Drawing Figure

DETECTION AND INDICATION DEVICE

BACKGROUND OF THE INVENTION

This invention relates to a device for the detection and indication of the presence of electrically conductive particles in a stream of fluid, particularly in an oil supply line.

Indicators for detecting blockage of filter pores by fine particles are known in which the pressure difference between supply and discharge flows is indicated by a pressure difference valve. Significant pressure differences are produced only when a certain proportion of the filter pores are blocked by particles, usually fine particles, and where large particles are involved which do not necessarily enter the pores of the filter, this type of indicator is not sufficiently effective.

In an installation such as a hydraulic system, in which oil is passed through pumps and other components with moving parts, defects or heavy wear usually result in the production of metal detritus or particles which enter the oil stream. These particles, which may be either fine or large according to the nature of the defect in the component are removed by the normal filtration device in the oil line. Unless there is produced a quantity of fine metallic particles sufficient to cause substantial blockage of filter pores, known indicators dependent on pressure differences are not sufficiently sensitive to provide early warning of the presence of material resulting from excessive wear or drainage to components such as pumps.

The present invention seeks to provide a device which will give an early warning of the presence of electrically conductive particles, such as metal detritus in an oil or other fluid stream.

SUMMARY OF THE INVENTION

According to the present invention, an indicating device for detecting electrically conductive particles in a non-conductive fluid, comprising a first electrical pole member constituted by means defining at least a portion of a flow-passage for the fluid having an inlet and an outlet, a filter element arranged in the flow-passage to intercept flow between inlet and outlet and having an entry surface exposed to the flow, a second electrical pole member located adjacent the entry surface and electrically insulated from the first pole member, a gap between first and second pole members dimensioned and located so as to permit bridging of the gap by accumulation in the gap of conducting particles, and an electrical circuit connecting first and second pole members to an electrically operated warning device, the circuit being closed when the gap is bridged by conductive particles. Preferably the means defining at least a portion of the flow passage is a housing assembly in which is located means for supporting a filter element. The means for supporting a filter element is preferably a support member made from an electrically insulating material, such as rubber or plastics material, which is sufficiently resilient to grip the filter element firmly and also to grip a portion of the housing assembly and thereby hold the filter in the desired position.

Conveniently, the support member, which can be a moulded ring, is also adapted to carry a metal detector ring mounted on the periphery of the mounted ring. The detector ring is thus electrically insulated from the housing assembly, which is connected to the electrical circuit of the warning device to form the first pole.

Preferably the housing assembly includes a gland in the wall through which passes an insulated conductor terminating within the housing in a contact which presses against the detector ring thus connecting the detector ring to the electrical circuit to form the second pole.

The detector ring may be located in the housing assembly more or less co-axially with the bore thereof and may be of an outside diameter smaller than this bore so as to leave between the outer surface of the detector ring and the inner surface of the bore of the housing assembly a gap for permitting accumulation of particles when in service.

Preferably the housing assembly is so constructed as to permit removal of the support member, detector ring and filter element. Thus the housing assembly may comprise an annular body member, and a detachable locating member, the locating member including means for mounting the support member thereon and locating the support member in a pre-determined position within the housing assembly.

The locating member is preferably a ring including a bore co-axial with the outlet pipe and having tubular extension of the bore which extends into the housing body.

The support member is preferably provided with a tubular extension which fits firmly into the extension of the locating member and is preferably provided with an annular groove into which a tubular filter element can be fitted. The support member also may serve to provide a seal between the inlet pipe and outlet pipe whereby all the fluid in the flow passage is constrained to pass through the filter element.

The size of the gap depends upon the size and number of conductive particles which enter the fluid and are transportable thereby. This is a matter which can be determined readily by those skilled in the art.

The invention can also be utilised in a modified construction in which the second pole member is associated with the filter element e.g., a detector ring located on this filter, which acts as an electrical insulator, other arrangements being made for mounting and seating the filter in this housing.

In another construction the second pole member may be a pin or stud in an insulating mounting in the wall of the housing and provided with an electrical conductor, the insulating mounting also being arranged to act as a gap which can be bridged by the particles. A pin may also be arranged by suitable mounting to provide a gap between it and the housing.

The invention is not restricted to a tubular form of filter element and a disc type of filter element can be used with a detector member such as a ring, plate or pin located at a suitable distance from the filter surface to provide a gap.

The gap can be located at a position where gravity assists in the accumulation of detritus.

BRIEF DESCRIPTION OF THE DRAWINGS

One embodiment of a device in accordance with the invention is now described with reference to the accompanying drawing which illustrates in cross-section a filtration arrangement in an oil supply line of a hydraulic system.

DESCRIPTION OF A PREFERRED EMBODIMENT

Figure 1:
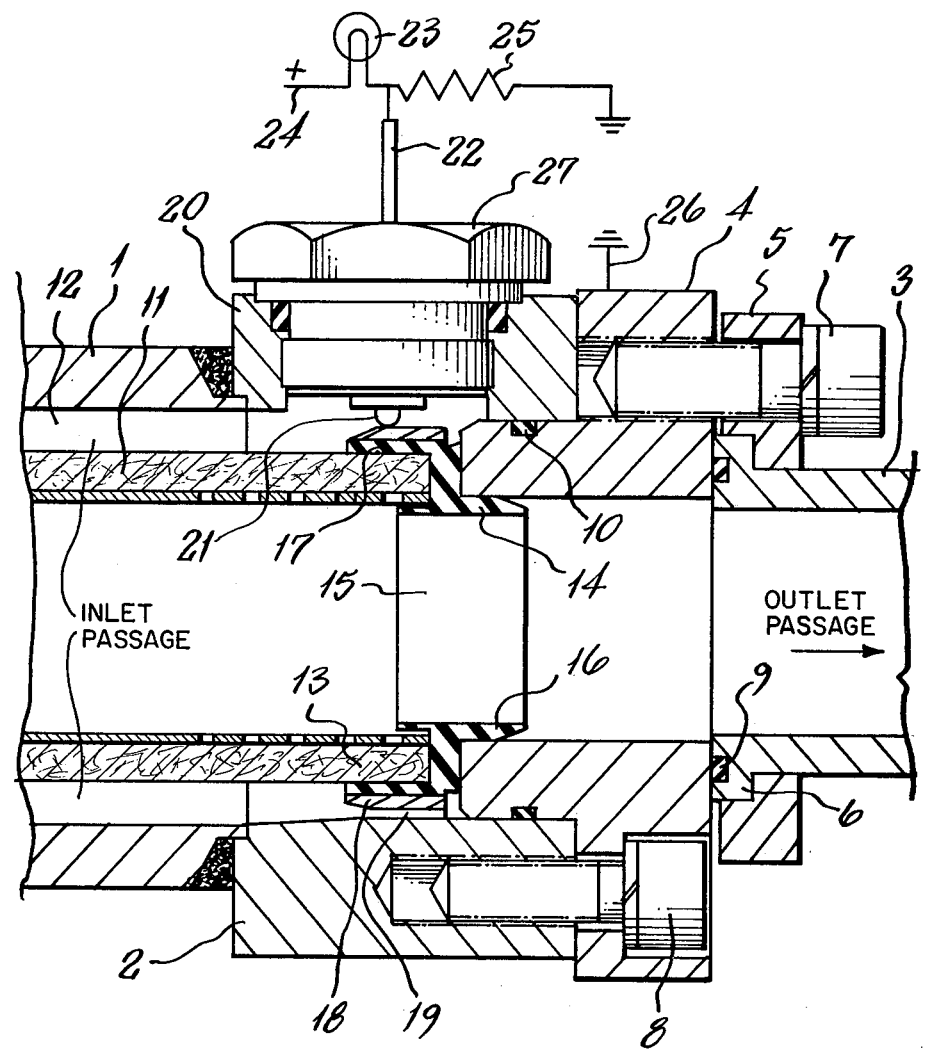

A pipe 1 for conveying oil from a source of supply is welded to a housing 2 and an outlet pipe 3 is releasably secured to a locating ring 4 by means of a collar 5 bearing on the flange 6 and screws 7.

Locating ring 4 is releasably secured to the housing 2 by screws 8. Sealing rings 9 and 10 maintain oil tightness.

Co-axially in the pipe 1 is located a tubular filter member 11 having one end (not shown) closed. An annular flow passage 12 is thus formed between the pipe 1 and the filter member 11 and terminates within the housing 2. The end portion 13 extends into the housing 2 and is there received in and supported by an electrically insulating support ring 14 sealingly engaging locating ring 4. Access for cleaning or replacing the filter member 11 is by releasing locating ring 4.

The support ring 14, which is of an oil resistant rubber or plastics material, is provided with a wide bore 15 so as to avoid unduly restricting oil flow, an axial extension 16 firmly engaging the bore of the locating ring 4, and an annular channel position 17 sealingly engaging the end portion 13 of the filter element 11. The locating ring 4 and the support ring 14 form a closure for the flow passage 12 so that oil is forced to pass through the filter element 11.

On the outer circumference of the support ring 14 is a metal detector ring 18 which is thus electrically insulated from the housing 2 and the locating ring 4 and is adjacent the outer or entry surface of the filter element 11. Between the detector ring 18 and wall of the housing 2 is a gap 19 which is sufficiently narrow to permit a build up of particles to bridge this gap in at least one small area.

A gland 20 is provided in the wall of the housing 2 having a gland nut 27 carrying an insulated contact 21 which engages the detector ring 18, and which is connected to an insulated electrical lead 22. A warning lamp 23 is connected to an electrical supply line 24 and through a resistance 25 to earth, and the lead 22 is connected between the lamp 23 and the resistance 25. The housing 2 is connected to earth through the oil pipe as a whole but a direct connection 26 to earth can be made if desired.

In use, oil flows through flow passage 12 and passes through the filter member 11, the bore 15, and thus into the outlet pipe 3. Particles are trapped in the passage 12, the finer ones in the filter material, and the larger, heavier, electrically conductive particles are swept into the gap 19 which is dimensioned so as to be bridged by a small accumulation of such particles. These particles are derived from wear or abrasion of machine parts, and are predominantly metallic.

In normal operation, current is supplied to the lamp 23 which is connected to earth through the resistor 25 so that the filament glows only faintly, thus indicating that the electrical circuit is alive. When the gap 19 has been bridged by one or more metallic particles, electrical current is able to flow between the detector ring 18 and the housing 2 which is connected to earth, thus short circuiting the resistor 25. The lamp 23 then glows brightly thereby giving warning that metallic particles, indicative of damage to working parts of the hydraulic system, are present in the oil supply.

Instead of a lamp 23, a warning device which is audible, such as a bell, or a combination of both lamp and bell can be used. The resistor connection to earth 25 can be omitted, in which case the lamp will be illuminated only when the gap 19 has been bridged.

The arrangement of a suitably dimensioned gap 19 at the end of the flow passage 12 provides an environment in which, due to a locally reduced rate of oil flow, accumulation of heavier particles can occur, particularly at the lowest point. This is an important consideration in giving warning early enough to enable action to be taken to prevent a major breakdown in a faulty component. A gap which is too wide, will, obviously, require a considerable time to become bridged, and this will give insufficient warning.

The filter element 11 can be removed and the gap 19 cleaned by releasing screws 8 and withdrawing the locating ring 4 together with the support ring 14, detector ring 18 and filter element 11 gripped in the annular channel portion from the housing 2. If necessary, the screws 7, collar 5 and pipe 3 may also be removed.

Whilst the invention has been described with particular reference to liquids, it is also applicable to gaseous fluids in which have entrained therein conducting particles, for example, fine metal powders or possibly carbon dust.

The detection of metal particles in an oil system at a sufficiently early stage may enable timely remedial action to be taken in respect of defects or premature wear in mechanical components of the system, and thereby avoid an unexpected breakdown.

We claim:

1. An indicative device for detecting electrically conductive particles in a non-conductive fluid comprising, a flow passage for a fluid including means defining an inlet passage, means defining an outlet passage connected to said inlet passage, electrical means connected to said inlet passage means to constitute a first pole member therewith, a filter element, said filter element having an entry surface for the fluid flow, support means of electrically insulative material, said support means concentrically mounting said filter element within said inlet passage so that all said fluid is constrained to pass from said inlet passage through said entry surface of said filter element to said outlet passage, said support means including a portion engaging said entry surface, a second electrical pole member, said second electrical pole member supported on said portion of said support means intermediate the entry surface of said filter element and the internal surface of said inlet passage means to define a gap of a predetermined dimension to enable build-up of said electrically conductive particles therein, and an electrical circuit connecting said first and second pole members to an electrically operated warning device, said circuit being closed when said gap is bridged by conductive particles.

2. A device according to claim 1 including a housing assembly having an annular body member secured to said means defining said inlet passage means, a detachable locating member secured to said annular body member, and wherein said support means of electrically insulative material is mounted within said locating member.

3. A device according to claim 1 wherein the second electrical pole member is a metal detector ring.

4. A device according to claim 3 wherein the support means of electrically insulative material is a resilient ring adapted to grip the filter element and to carry on its peripheral surface the metal detector ring co-axially with the flow passage, and wherein the locating member includes a bore coaxial with said annular member the said support means having a tubular extension resiliently engageable with the tubular extension of the bore of the locating member.

5. A device according to claim 4 wherein the detector ring is of an outside diameter smaller than the bore of the annular body member whereby there is formed between the outer surface of the ring and the bore, a gap of size suitable for permitting, in use, accumulation of particles.

6. A device according to claim 3 wherein a wall of the annular body member includes a gland having mounted thereon an insulated electrical contact located to press against the detector ring and an insulated electrical conductor for connecting the contact to the electrical circuit.

7. A device according to claim 1 wherein the second electrical pole member is a pin.

8. A device according to claim 1 wherein the second electrical pole member is supported by said filter element.

* * * * *